(12) United States Patent
Gerhardt et al.

(10) Patent No.: US 8,640,730 B2
(45) Date of Patent: Feb. 4, 2014

(54) VARIABLE RESISTANCE FLUID CONTROLLER

(75) Inventors: Geoff C. Gerhardt, Millbury, MA (US); Christopher C. Charlton, Benicia, CA (US)

(73) Assignee: Waters Technologies Corporation, Milford, MA (US)

( * ) Notice: Subject to any disclaimer, the term of this patent is extended or adjusted under 35 U.S.C. 154(b) by 1073 days.

(21) Appl. No.: 11/814,423

(22) PCT Filed: Jul. 18, 2006

(86) PCT No.: PCT/US2006/001563
§ 371 (c)(1),
(2), (4) Date: Feb. 22, 2008

(87) PCT Pub. No.: WO2006/078633
PCT Pub. Date: Jul. 27, 2006

(65) Prior Publication Data
US 2008/0283134 A1 Nov. 20, 2008

Related U.S. Application Data

(60) Provisional application No. 60/645,802, filed on Jan. 21, 2005.

(51) Int. Cl.
*E03D 5/01* (2006.01)
*F16K 17/38* (2006.01)
*B01F 5/00* (2006.01)
*G01N 30/02* (2006.01)

(52) U.S. Cl.
USPC .............. 137/468; 137/564.5; 137/599.12; 137/601.18; 222/386.5; 222/389; 73/61.56

(58) Field of Classification Search
USPC .............. 137/205.5, 208, 564.5, 565.12, 5, 137/599.12, 601.18, 457, 468; 222/386.5, 222/389; 73/61.56
See application file for complete search history.

(56) References Cited

U.S. PATENT DOCUMENTS 2,069,261 A * 2/1937 Monnet .................. 451/446
2,134,778 A 11/1938 Clarke
(Continued)

FOREIGN PATENT DOCUMENTS

DE 199 14 358 A1 10/2000
JP 07-306192 A 11/1995
WO 0205006 A1 1/2002

OTHER PUBLICATIONS

Chervet JP et al., "Recent Advances in Capillary Liquid Chromatography, Delivery of Highly Reproducible Microflows", LC-GC International (Liquid and Gas Chromatography), Eugene, OR, US, vol. 4, No. 11, Jan. 1, 1991, 8 pages (pp. 32-40).

(Continued)

*Primary Examiner* — Craig Schneider
*Assistant Examiner* — Atif Chaudry
(74) *Attorney, Agent, or Firm* — Schmeiser, Olsen & Watts, LLP

(57) ABSTRACT

A fluid controller apparatus controls fluid flow, such as a solvent gradient flow, in a chromatography system. An apparatus includes a fluid-gradient controller having a fluid reservoir for containing a pump fluid and a pumping device connected to the fluid reservoir for receiving the pump fluid. The pumping device is in fluid communication with parallel-configured first and second solvent lines. The first and second solvent lines each contain a restrictor element and a solvent reservoir. During operation, the pumping device causes the pump fluid to flow through the first and second solvent lines in relation to their respective restriction devices. The pump fluid displaces solvent within the solvent reservoirs. The displaced solvent is mixed to form a solvent gradient.

21 Claims, 4 Drawing Sheets

(56) References Cited

U.S. PATENT DOCUMENTS

| | | | |
|---|---|---|---|
| 2,379,109 A | | 6/1945 | Shaw |
| 3,521,671 A | * | 7/1970 | Handeland ................. 137/564.5 |
| 3,593,917 A | * | 7/1971 | Buisson ........................ 236/98 |
| 4,239,623 A | * | 12/1980 | Schrenker ................... 210/96.1 |
| 4,497,438 A | * | 2/1985 | Bonne .......................... 237/8 R |
| 4,962,662 A | | 10/1990 | Berger |
| 5,273,070 A | * | 12/1993 | Chili et al. ............... 137/599.15 |
| 5,630,706 A | | 5/1997 | Yang |
| 5,777,213 A | * | 7/1998 | Tsukazaki et al. ........... 73/61.52 |
| 5,797,520 A | * | 8/1998 | Donahue ................... 222/386.5 |
| 6,296,452 B1 | | 10/2001 | Caren |

OTHER PUBLICATIONS

Rapp et al., "Liquid Flow in Capillary (Electro)chromatography: Generation and Control of Micro- and Nanoliter Volumes", Journal of Separation Science, vol. 26, No. 6-7, May 2003, Wiley-VCH Verlag DE, 18 pages (pp. 453-470).

European Search Report, dated Aug. 16, 2010, of counterpart European Application No. EP 06 71 8616.

Official Action mailed Jan. 10, 2012 in Japanese Patent Application No. 2007-552209.

* cited by examiner

VARIABLE RESISTANCE FLUID CONTROLLER

CROSS REFERENCE TO RELATED APPLICATIONS

This application is the National Stage of International Application No. PCT/US2006/001563, filed on Jan. 18, 2006, which claims priority from U.S. Provisional Patent Application No. 60/645,802 filed on Jan. 21, 2005. The entire contents of these applications are incorporated herein by reference.

FIELD OF THE INVENTION

This invention relates generally to control of fluid in analytical processes and more particularly to fluid control such as the formation of a solvent gradient in nano-scale chromatography.

BACKGROUND OF THE INVENTION

The recent interest in nano-scale chromatography (<1 µL/min flow rates) has prompted HPLC instrument manufacturers to try to develop pumps capable of delivering lower flow rates. Unfortunately, typical analytical-scale HPLC pump technology does not scale well to these low flow rates as the constant-flow open-loop analytical-scale pumps typically used for analytical-scale chromatography (0.1-5 mol/min) are good flow sources above ~0.1 µL/min, but below these flow rates, inaccuracies due to solvent compression and seal fitting or check-valve leakage compromise their flow accuracy.

Multi-component mobile phase/solvent mixtures are routinely used in HPLC for isocratic separations, where the composition of the mobile phase/solvent mixture is kept constant. The composition may be prepared by the user or generated on-demand by the pump or solvent delivery system. However, in gradient separations the composition of the mobile phase/solvent mixture is changed in a continuous manner during the course of the analysis. Generation of this solvent gradient is typically achieved in one of two ways: 1) by pre-mixing mobile phase components on the low-pressure suction side of the pump, or 2) by employing a series of high pressure pumps to deliver the requisite number of components to a high-pressure mixture.

While low pressure gradient formation has the advantage of requiring a single high-pressure pump and a series of inexpensive solvent proportioning valves (for low-pressure solvent mixing), low pressure gradient formation has several disadvantages. Unfortunately, as the rate of solvent delivery is decreased to flow rates typical for micro-bore, capillary or nano-scale chromatography (i.e. <100 µL/min), the pump head volume of the high pressure pump (typically <50 µL) comprises too large a fraction of the overall elution volume. This causes the loss of gradient resolution. For example, for a typical capillary-scale LC gradient separation where a flow rate of 10 µL/min is used, assuming a pump head volume of 50 µL, the gradient composition would change every 5 minutes rather than the near continuous gradient resolution required to achieve a good gradient LC separation. As such, for applications using lower flow rate separations, high pressure gradient mixing has been used.

Traditional plunger displacement pumping systems have been successful in delivering stable, accurate flows in the normal-scale and micro-scale high performance liquid chromatography (HPLC) regimes. While normal-scale HPLC is performed with mobile phase flow rates of about 0.1-5.0 mL/min and micro-scale HPLC is performed with mobile phase flow rates of about 1-100 µL/min, nano-scale HPLC requires mobile phase flow rates in about the 50-500 mL/min range. Plunger displacement pumping systems can not deliver nano-scale HPLC flow rates with reliability and accuracy.

However, in nano-scale LC, where flow rates of about 200 nL/min are typically used, each high pressure pump used must be capable of delivering as low as 10 nL/min (i.e. 5% of the total 200 nL/min flow rate) to produce a binary compositional gradient of 95%/5% to 5%/95%. Since current pumping technologies meter flow delivery by measuring the displacement of a plunger, this is extremely difficult to achieve. Although metering flow by measuring plunger displacement is possible in the >1 µL/min regime (because seal/fittings leak rates will likely be an order of magnitude less than the bulk flow rate), this is not the case when pumping 10's of nL/min (because leak rates may be of the same order of magnitude as the pump flow rate). Additionally because traditional plunger/seal pumping systems have not been miniaturized sufficiently, the fluidic capacitance of current pump head designs tend to create additional difficulties in predicting the flow generated in the presence of changing pump pressure. Accordingly, presently available flow sensors have inadequate reliability, precision and accuracy for use in the 10's of nL/min scale liquid chromatography applications.

SUMMARY OF THE INVENTION

The apparatus according to the invention advantageously solves problems associated with displacement-metered high-pressure pumps by providing a novel fluid and gradient controller which uses solvent lines having variable restrictors that could be used in any of various LC flow regime. A parallel solvent line configuration advantageously provides the ability to generate gradient flow in the nano-scale LC regime by controlling the ultimate flow rate delivered by the high-pressure pump in spite of solvent compression in the pump head and/or pump head leakage.

According to the invention, a fluid gradient control apparatus includes a pump fluid reservoir for containing and pumping a pump fluid. A pump device is connected to the pump fluid reservoir for receiving the pump fluid. In a first illustrative embodiment the pump device is in fluid communication with a first solvent line and a second solvent line is connected in parallel. A variable restriction device and a solvent reservoir are provided within each parallel solvent line. The pump device is operated to cause the pump fluid to flow through the respective parallel solvent lines subject to respective resistance provided by variable restriction devices within each solvent line. The pump fluid causes a solvent within each respective solvent reservoir to be pumped from the solvent reservoir as a function of the resistance provided by the respective restriction device. The pumped solvents form a gradient composition that is delivered via a mixing tee to a chromatographic system.

In a further illustrative embodiment, a method is provided for implementing a fluid gradient flow in a Liquid Chromatography (LC) system via in-line restrictor elements within parallel solvent lines. The LC system includes a fluid gradient controller apparatus having a pump fluid reservoir containing a pump fluid, a pump device, a variable restriction device and solvent reservoir within each parallel solvent line. A mixing tee delivers a formed solvent gradient to an analytical column. The method includes operating a pumping device to cause the pump fluid to flow through the variable restriction device and controlling the at least one variable restriction device to cause the pump fluid to flow responsive to the variable restriction devices. The solvent fluid gradient is generated by the pump fluid displacing the respective solvents within the solvent reservoirs thereby forming a solvent gradient that is delivered via a mixing tee to the chromatographic system.

The embodiments according to the present invention advantageously provide gradient control in the nano-scale regime by implementing a mechanism that overcomes the problems of solvent compression in the pump head. The problems of pump head leakage are overcome on the high pressure side of a gradient system.

BRIEF DESCRIPTION OF DRAWINGS

The foregoing and other features and advantages of the present invention will be better understood from the following detailed description of illustrative embodiments, taken in conjunction with the accompanying drawings in which.

DETAILED DESCRIPTION OF THE INVENTION

Figure 1:
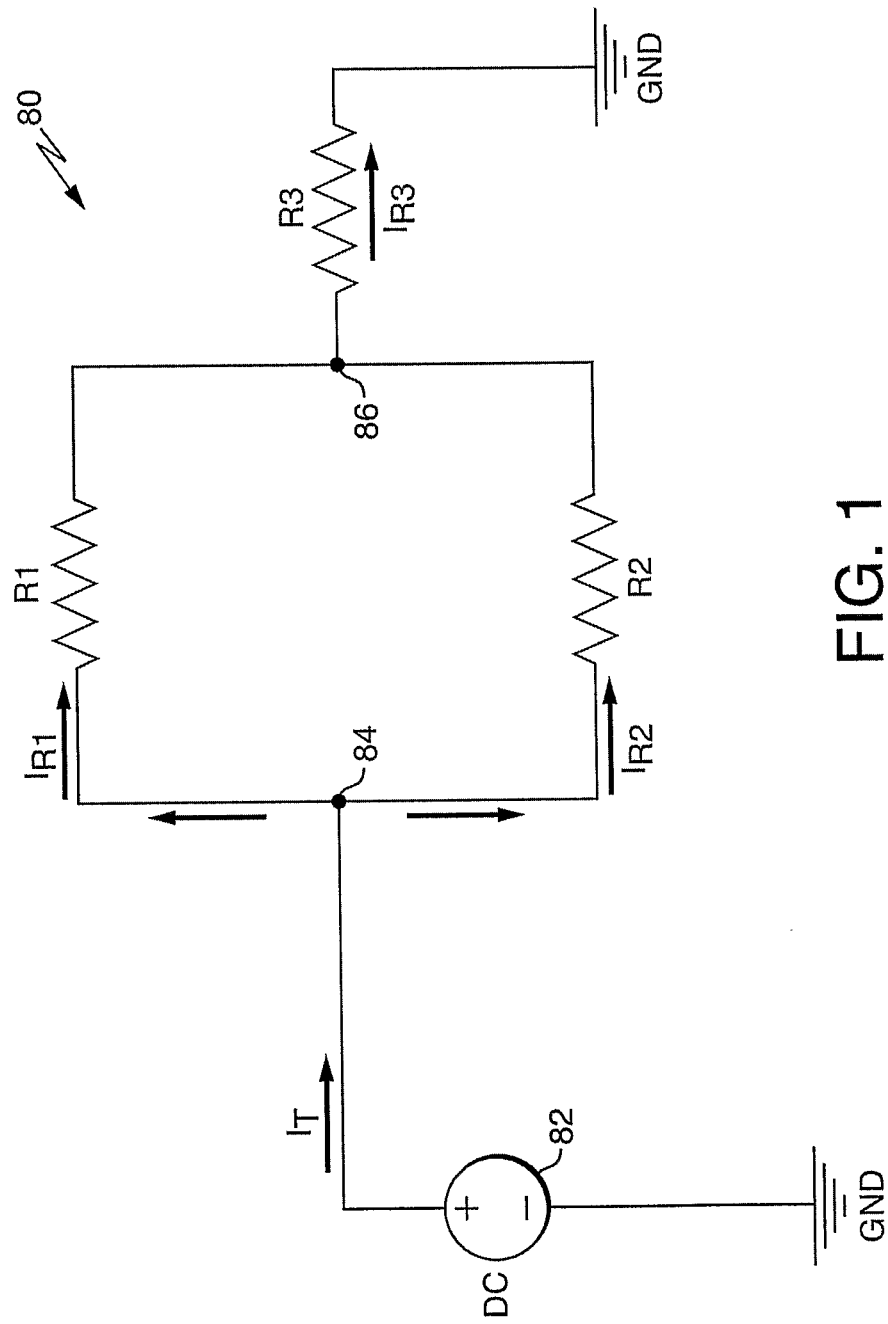
FIG. 1 is a schematic diagram modeling a fluid gradient controller apparatus, in accordance with an exemplary embodiment of the invention.

For illustrative purposes, the present invention can be modeled using a simple electronic circuit. Referring to FIG. 1, a simple resistance electronic circuit 80 represents the fundamental construction of the gradient controller apparatus according to the invention. The system model includes a DC power source 82 connected to a ground potential and a first common node 84. It should be appreciated that DC power source 82 is used to model the combination of pump fluid reservoir and pump as described in an illustrative embodiment hereinafter. The first common node 84 is further connected to a first resistor R1 and a second resistor R2 which are connected in parallel, and to a second common node 86. It should be appreciated that the first resistor R1 is used to model the combination of a first variable restrictor and first solvent reservoir and the second resistor R2 is used to model the combination of a second variable restrictor and second solvent reservoir as described hereinafter. The second common node 86 is used to model a mixing tee in a gradient system. The second common node 86 is connected to a third resistor R3 which is further connected to ground potential 226, thus completing the circuit. It should be further appreciated that third resistor R3 is used to model analytical column 116. In the illustrative models completion of resistance electronic circuit 80 causes a total current $I_T$ to flow (as is conventionally known) from DC power source 82. The total current flow $I_T$ is shown flowing from DC power source 82 into the first common node 84, where total current $I_T$ is divided into a first resistor current flow $I_{R1}$ and a second resistor current flow $I_{R2}$. The first resistor's current flow $I_{R1}$ is shown flowing through first resistor R1 and into second common node 86. Similarly, the second resistor current flow $I_{R2}$ is shown flowing through second resistor R2 and into second common node 86 where the second resistor current flow $I_{R2}$ and first resistor current flow $I_{R1}$ combine to create a third resistor current flow $I_{R3}$. The third resistor current flow $I_{R3}$ flows through third resistor R3 to ground.

In the illustrative model, if the total current $I_T$ is fixed and maintained throughout resistance electronic circuit, the first resistor current flow $I_{R1}$ and second resistor current flow $I_{R2}$ can be varied simply by adjusting the values of first resistor R1 and second resistor R2, respectively. The first resistor current flow $I_{R1}$ and second resistor current flow $I_{R2}$ can be controlled independently without affecting the total current $I_T$. Similarly, in the case that a power supply having power range limitations is used, if the values of first resistor R1 and second resistor R2 are much less than the value of third resistor R3, or if the value of the equation $1/(1/R1+1/R2)$ is maintained constant, then the current flowing through first resistor R1 and second resistor R2 can be manipulated without appreciably changing the total current $I_T$. The principles of this illustrative model are applicable to an illustrative implementation of a gradient controller system as described hereinafter.

Figure 2:
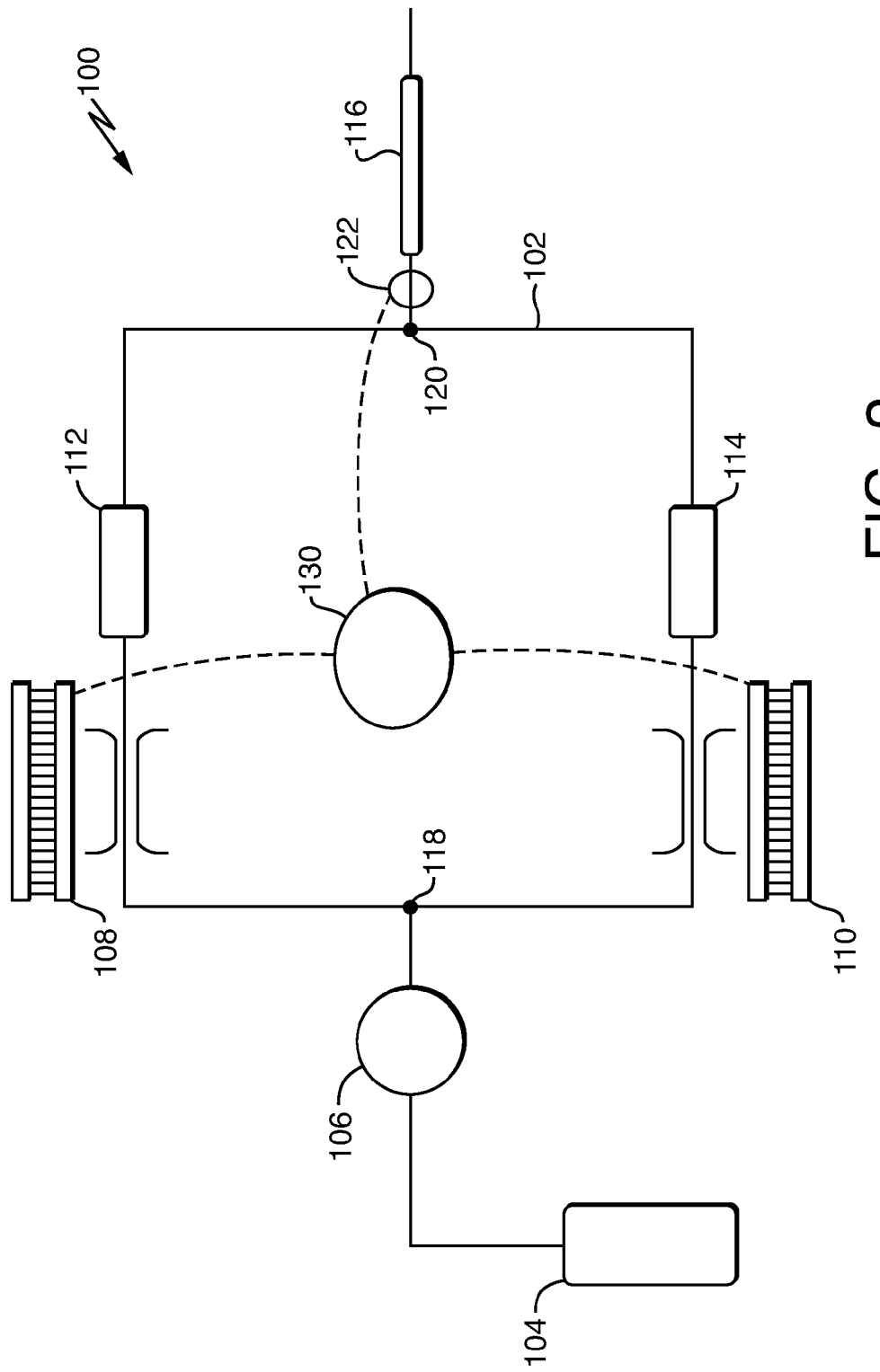
FIG. 2 is a block diagram representing a fluid gradient controller apparatus, in accordance with an exemplary embodiment.

Referring now to FIG. 2, a representation of a gradient controller apparatus 100 according to the invention is illustrated. In a first illustrative embodiment a parallel fluid resistance network 102 comprises a pump fluid reservoir 104, a pump 106 first solvent line having a first variable restrictor 108, and a second solvent line having a second variable restrictor 110. In this illustrative embodiment the first and second variable restrictors 108, 110 are temperature controlled variable restrictors such as Peltier devices used to provide temperature changes to change the viscosity (i.e., resistance) of the pumping fluid. Illustrative Peltier devices include Melcor Peltier CP 1.4-71-045L or the like. It is contemplated within the scope of the invention that other variable restrictor elements known in the art may be used such as a needle valve restrictor, or the like.

In the first solvent line the first variable restrictor 108 is in fluid communication with a first solvent reservoir 112. In the second solvent line the second variable restrictor 110 is in fluid communication with a second solvent reservoir 114. In operation the pump fluid reservoir 104 containing a pumping fluid is connected to the pump 106 or pressure source which is in fluid communication with a fluidic tee 118 or flow splitter to deliver pumping fluid to the first solvent line and second solvent line. The fluidic tee 118 is in fluid communication with the first solvent line 101 and the second solvent line 103, which are in fluid communication with the first variable restrictor 108 and second variable restrictor 110. The first variable restrictor 108 is in fluid communication with the first solvent reservoir 112 and the second variable restrictor 110 is in fluid communication with the second solvent reservoir 114. First solvent reservoir 112 and second solvent reservoir 114 are in fluid communication with a mixing tee 120. The mixing tee 120 is in fluid communication with an analytical column 116 via a gradient solvent line. The gradient solvent line can be optionally equipped with a compositional sensor 122 that is in communication with a system controller 130. The first and second variable restrictors 108, 110 can have preset restriction or can be in communication with the system controller 130 to selectively control and vary flow restriction.

According to the invention, if the pump 106 delivers a constant fluid flow to parallel fluid resistance network 102 (i.e. either by measuring the displacement of a plunger or a pressure source in a closed-loop feedback with a flow sensor or by other means), the flow of fluid through the first and second solvent lines that form the parallel fluid resistance network 102 may be controlled by varying the magnitude of first variable restrictor 106 and second variable restrictor 108. As the rate of flow of the mobile phase/solvent components change in response to the manipulation of the parallel fluid resistance network 102, the flow change will advantageously manifest itself as a composition change in the delivered mobile phase/solvent mixture from the respective solvent reservoirs 112, 114. Thus, according to this illustrative configuration the composition of the mobile phase/solvent flow can be controlled for gradient flow in the nano-scale LC regime.

Figure 3:
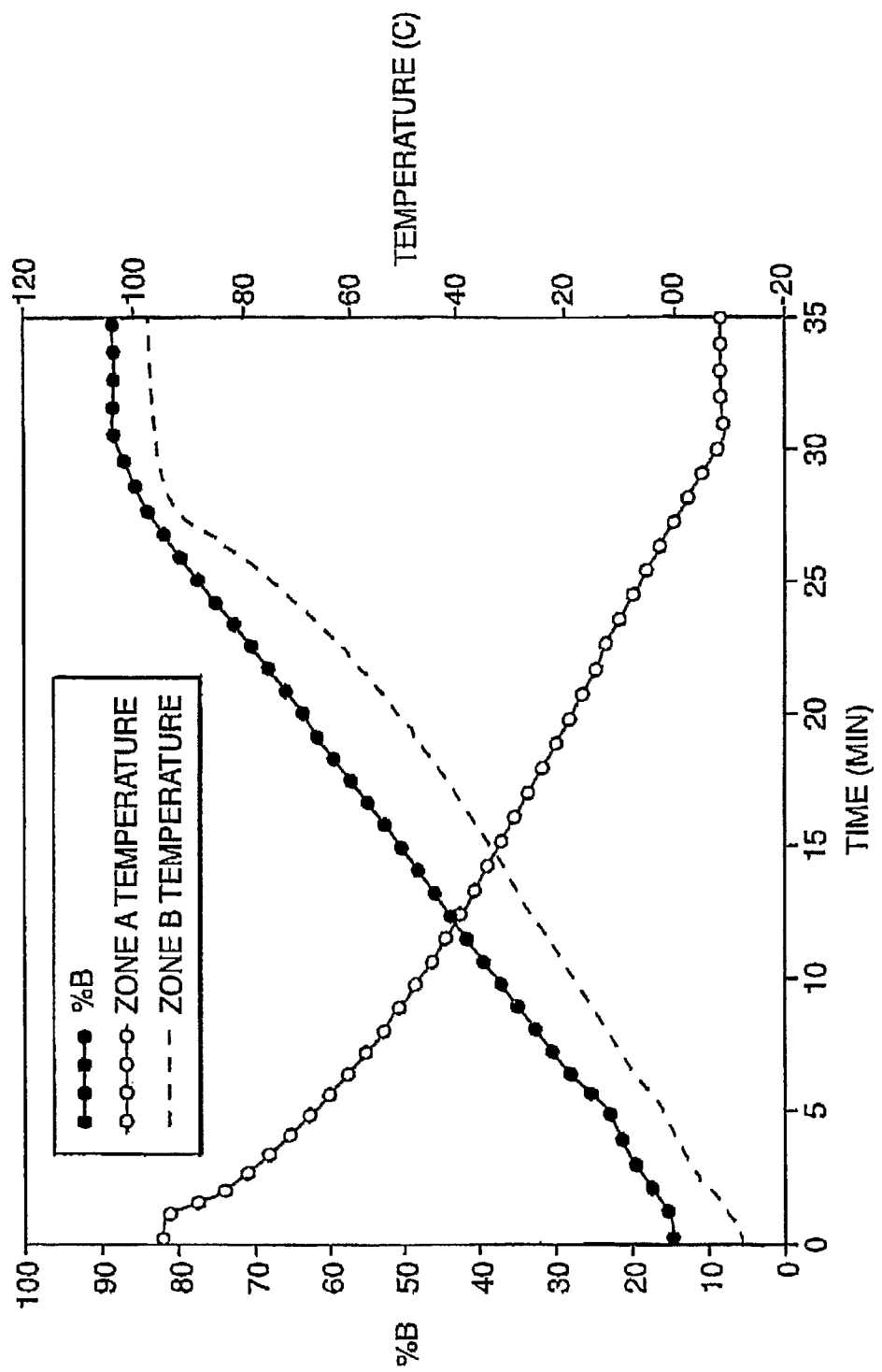
FIG. 3 is a graph showing the sample data obtained from tests using a device that models a fluid gradient controller apparatus, in accordance with the exemplary embodiment of the invention.

Referring to FIG. 3, data obtained from operation of a device having a parallel fluid resistance network 102 according to the invention is shown for illustrative purposes. In this illustrative example, however, Sensirion flow sensors (SLG1430-015) have been substituted in place of the first solvent reservoir 112 and second solvent reservoir 114 to measure the fluid flow through first variable restrictor 106 and second variable restrictor 108. The fluid used for this example was water and the % B element was defined as the fluid flow through second variable restrictor 108 divided by the sum of the fluid flow through first variable restrictor 106 and second variable restrictor 108 (i.e. % $B=I_{R2}/(I_{R1}+I_{R2})$). The first variable restrictor 106 and second variable restrictor 108, within this illustrative example, were temperature-controlled restriction elements which included thermoelectric controllers Microsemi controller EVB2816 for controlling the temperature. In this illustrative embodiment, by controlling the temperature of first variable restrictor 106 and/or second variable restrictor 108, the viscosity of the pump pushing fluid flowing through first variable restrictor 106 and/or second variable restrictor 108 may advantageously be manipulated to effect a variable fluidic resistance.

As can be seen from FIG. 3, compositional control of the fluid flowing through first variable restrictor 106 and second variable restrictor 108 can be adjusted from 10-90% using the restrictor temperatures from 10-95 C. Thus, it can be seen that in order to produce gradients of <10% B either greater restrictor temperature extremes could be used or a pump fluid could be used having a greater change in viscosity with temperature (e.g. a suitable polymer solution having a much larger viscosity change with temperature could be selected). It is contemplated within the scope of the invention that the pump fluid may not have to exit the gradient controller. In that case, a mechanical or diffusion boundary could be disposed between the pump fluid and the LC mobile phase component in the solvent reservoir, and pumping provided for redirecting and storing the pump fluid in pump fluid reservoir 104.

Figure 4:
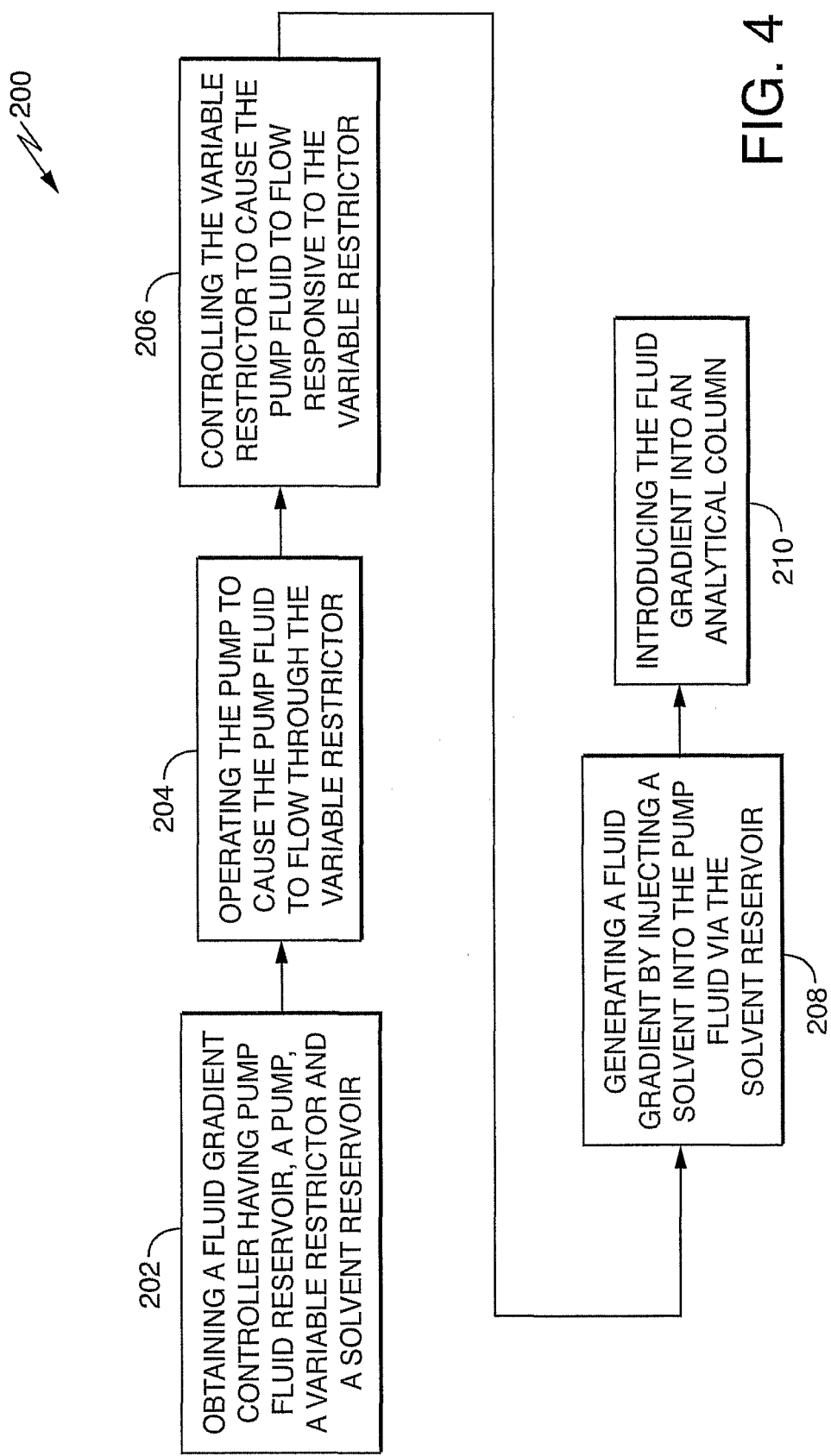
FIG. 4 is a block diagram describing a method for controlling a fluid gradient flow in a Liquid Chromatography (LC) system.

Referring to FIG. 4, a method 200 for controlling a fluid gradient flow in a Liquid Chromatography (LC) system is shown and includes configuring a fluid gradient controller apparatus 100, as shown in block 202. The fluid gradient controller apparatus 100 is arranged as described hereinabove and has a pump fluid reservoir 104 containing a pump pushing fluid. The fluid gradient controller apparatus 100 also includes a pumping device 106, a first variable restrictor 108, a second variable restrictor 110, a first solvent reservoir 112, a second solvent reservoir 114 and an analytical column 116. The pumping device 106 is operated to cause the pump fluid to flow from pump fluid reservoir 104 and through two or more variable restrictors, as shown in block 204. As described, the pump fluid flows from pumping device 106 into first tee 118 where the pump fluid flow splits into first and second solvent lines. The first solvent line directs the pump fluid into the first variable restrictor 108 and the second solvent line directs the pump fluid into second variable restrictor 110. As the pump fluid flows along the first and second flow solvent lines the first variable restrictor 108 and second variable restrictor 110 are controlled to cause the pump fluid to flow in a manner in response to first variable restrictor 108 and second variable restrictor 110, as shown in block 206.

In accordance with an illustrative embodiment, because the first variable restrictor 108 and second variable restrictor 110 are temperature-controlled restriction elements, pump fluid flow control may be accomplished by controlling the temperature, and thus the viscosity, of the pump fluid. As the temperature of the pump fluid decreases, the viscosity of the pump fluid increases and the pump fluid flow is slowed. It should be appreciated that the pump fluid flow through first variable restrictor 108 may be controlled independently from second variable restrictor 110.

As the pump fluid flows through first variable restrictor 108 and second variable restrictor 110, a fluid gradient is generated by the pump fluid displacing the solvents from the first solvent reservoir 112 and second solvent reservoir 114, respectively, as a function of the first and second variable restrictions, respectively, as shown in block 208. The displaced solvent flows from the first flow path and the second flow path in proportion to the restriction within the respective restriction elements. The displaced solvents are mixed via the second mixing tee 120 forming a fluid gradient. The fluid gradient is then introduced into analytical column 116, as shown in block 210. It is contemplated within the scope of the invention that the fluid gradient may be introduce into any chromatographic system.

Although first variable restrictor 106 and second variable restrictor 108 are temperature-controlled restriction elements, any of various restriction elements and/or methods suitable to the desired end purpose may be used.

The processing of at least a portion of the method in FIG. 4 may be implemented by a controller disposed internal, external or internally and externally to a fluid gradient controller apparatus 100. In addition, processing of at least a portion of the method in FIG. 4 may be implemented through a controller operating in response to a computer program. In order to perform the prescribed functions and desired processing, as well as the computations therefor (e.g. execution control algorithm(s), the control processes described herein, and the like), the controller may include, but not be limited to, a processor(s), computer(s) memory, storage register(s), timing interrupt(s), communication interface(s), and input/output signal interface(s), as well as combinations comprising at least one of the foregoing.

The invention may be embodied in the form of computer or controller implemented processes. The invention may also be embodied in the form of computer program code containing instructions embodied in tangible media, such as floppy diskettes, CD-ROMs, hard drives, and/or any other computer-readable medium, wherein when the computer program code is loaded into and executed by a computer or controller, the computer or controller becomes an apparatus for practicing the invention. The invention can also be embodied in the form of computer program code, for example, whether stored in a storage medium, loaded into and/or executed by a computer or controller, or transmitted over some transmission medium, such as over electrical wiring or cabling, through fiber optics, or via electromagnetic radiation, wherein when the computer program code is loaded into and executed by a computer or a controller, the computer or controller becomes an apparatus for practicing the invention. When implemented on a general-purpose microprocessor the computer program code segments may configure the microprocessor to create specific logic circuits.

Although the illustrative embodiments according to the invention show two solvent lines in parallel to each other for gradient control it should be appreciated by those skilled in the art that the instant invention can have one fluid control channel or have numerous solvent lines in parallel with each other that can form solvent gradients having two or more components. Likewise it should be appreciated by those skilled in the art that the gradient controller system according to the invention can use just one solvent line during the operation of the system to flush analytical devices attached to the gradient control device. It should be appreciated that structures other than a mixing tee can be used to select a variable restricted flow path for effecting gradient composition.

Although the illustrative embodiments according to the invention use a pump fluid to displace the solvent within a solvent reservoir it should be appreciated by those skilled in the art that physical components such as diaphragms or the like can separate the pump fluid from the solvents within the solvent reservoir. Likewise it should be appreciated by those skilled in the art that pump fluids of varying viscosities may be used to displace solvents within solvent reservoirs. Furthermore, it should be appreciated that pump fluids may be the combination of both fluids and solids.

While the invention has been described with reference to an illustrative embodiment, it will be understood by those skilled in the art that various changes, omissions and/or additions may be made and substantial equivalents may be substituted for elements thereof without departing from the spirit and scope of the invention. In addition, many modifications may be made to adapt a particular situation or material to the teachings of the invention without departing from the scope thereof. Therefore, it is intended that the invention not be limited to the particular embodiment disclosed for carrying out this invention, but that the invention will include all embodiments falling within the scope of the appended claims. Moreover, unless specifically stated any use of the terms first, second, etc. do not denote any order or importance, but rather the terms first, second, etc. are used to distinguish one element from another.

What is claimed is:

1. A fluid-controller apparatus comprising:
   a pump-fluid reservoir for containing a pump fluid;
   a pumping device connected to the pump-fluid reservoir for pumping the pump fluid;
   at least one variable-restriction device connected to the pumping device, the at least one variable-restriction device comprising a temperature-controlled restriction element, wherein, when the pumping device is operated, the pumping device causes the pump fluid to flow through the at least one variable-restriction device;
   at least one solvent-fluid reservoir, for containing a solvent fluid comprising at least one solvent, connected to the at least one variable-restriction device; and
   a chromatographic column in fluidic communication with the at least one variable-restriction device to receive the solvent fluid displaced by the pump fluid in relation to restriction provided by the at least one variable-restriction device.

2. The fluid-controller apparatus of claim 1, wherein the pumping device is connected to the at least one variable-restriction device via a fluidic tee.

3. The fluid-controller apparatus of claim 1, wherein the at least one variable-restriction device comprises a first variable-restriction device, associated with a first solvent line, and a second variable-restriction device, associated with a second solvent line.

4. The fluid-controller apparatus of claim 3, wherein the at least one solvent-fluid reservoir comprises a first solvent-fluid reservoir, connected to the first variable restriction device, and a second solvent-fluid reservoir, connected to the second variable restriction device.

5. The fluid-controller apparatus of claim 4, wherein the fluid controller apparatus provides a solvent gradient for the chromatographic column.

6. The fluid-controller apparatus of claim 4, wherein the first variable-restriction device and the first solvent-fluid reservoir are connected in parallel to the second variable-restriction device and the second solvent-fluid reservoir.

7. The fluid-controller apparatus of claim 3, wherein one of the first variable-restriction device and second variable-restriction device comprises a mechanical-restriction element.

8. The fluid-controller apparatus of claim 1, wherein the pumping device pumps the pump fluid at a flow rate of less than one microliter per minute ($\mu$L/min).

9. A method for forming a fluid gradient in a liquid-chromatography system, comprising:
   providing a fluid-gradient controller apparatus comprising a first variable-restriction device, in communication with a first solvent reservoir containing at least a first solvent, and a second variable-restriction device, in communication with a second solvent reservoir containing at least a second solvent;
   pumping at least one pump fluid through the first and second variable-restriction devices, thereby displacing the first and second solvents; and
   varying a first flow restriction and a second flow restriction respectively provided by the first variable-restriction device and the second variable-restriction device to mediate a gradient of the displaced first and second solvents, wherein varying the first flow restriction occurs in response to changes in temperature produced by the first variable-restriction device.

10. The method for controlling a fluid gradient of claim 9, wherein the first variable-restriction device is separate from and connected to the first solvent reservoir and the second variable-restriction device is separate from and connected to the second solvent reservoir.

11. The method for controlling a fluid gradient of claim 9, wherein the first variable-restriction device and the first solvent reservoir are connected to the second variable-restriction device and the second solvent reservoir in parallel.

12. The method for controlling a fluid gradient of claim 9, further comprising combining the displaced first and second solvents, and flowing the combined solvents through an analytical column.

13. The method for controlling a fluid gradient of claim 9, wherein the pumping produces a flow rate of the pump fluid of less than one microliter per minute ($\mu$L/min).

14. A liquid-chromatography apparatus, comprising:
   a chromatographic column;
   means for variably restricting a first flow path, the means for variably restricting the first flow path comprising a variable-restriction component that varies restriction in response to changes in temperature;
   means for variably restricting a second flow path;
   means, responsive to the means for variably restricting the first flow path, for displacing a first solvent;
   means, responsive to the means for variably restricting the second flow path, for displacing a second solvent;
   means for combining the displaced first and second solvents; and
   means for delivering the combined first and second solvents to the chromatographic column.

15. The apparatus of claim 14, further comprising means for delivering a pump fluid to the means for variably restricting the first flow path.

16. The apparatus of claim 15, wherein the means for delivering the pump fluid comprises a pump.

17. The apparatus of claim 15, wherein the means for delivering the pump fluid delivers the pump fluid at a flow rate of less than one microliter per minute (µL/min).

18. The apparatus of claim 14, wherein the means for displacing the first solvent comprises a pump fluid that flows through the first flow path.

19. The apparatus of claim 18, wherein the means for displacing the first solvent further comprises a reservoir that contains at least some of the first solvent.

20. The apparatus of claim 14, wherein the means for combining comprises a mixing tee.

21. A liquid chromatography system, comprising:
- a pumping device pumping liquid at a flow rate of less than one microliter per minute (µL/min);
- first and second solvent reservoirs, each solvent reservoir containing a solvent;
- a flow splitter directing a first portion of the pumped liquid over a first flow path to the first solvent reservoir and a second portion of the pumped liquid over a second flow path to the second solvent reservoir;
- a first variable restrictor disposed in the first flow path between the pumping device and the first solvent reservoir to variably restrict a flow of the first portion of liquid and thereby a rate of displacement of the solvent in the first solvent reservoir by the first portion of liquid; and
- a second variable restrictor disposed in the second flow path between the pumping device and the second solvent reservoir to variably restrict a flow of the second portion of liquid and thereby a rate of displacement of the solvent in the second solvent reservoir by the second portion of liquid;
- a flow combiner coupled to receive and combine the solvents displaced from the first and second solvent reservoirs and to produce a solvent gradient therefrom; and
- a chromatographic column in fluidic communication with the flow combiner to receive the solvent gradient therefrom.

* * * * *